(12) United States Patent  (10) Patent No.: US 7,284,281 B2
Huh  (45) Date of Patent: Oct. 23, 2007

(54) WELDING HELMET HAVING CARTRIDGE COUPLING STRUCTURE

(75) Inventor: Moon Young Huh, Seoul (KR)

(73) Assignee: Otos Tech Co., Ltd. (KR)

( * ) Notice: Subject to any disclaimer, the term of this patent is extended or adjusted under 35 U.S.C. 154(b) by 245 days.

(21) Appl. No.: 11/053,977

(22) Filed: Feb. 9, 2005

(65) Prior Publication Data

US 2006/0185052 A1  Aug. 24, 2006

(51) Int. Cl.
A61F 9/06 (2006.01)
(52) U.S. Cl. ............................................................. 2/8
(58) Field of Classification Search ............. 2/8.1–8.5, 2/8.7, 8.8, 427, 429; 128/206.23; 219/147
See application file for complete search history.

(56) References Cited

U.S. PATENT DOCUMENTS

| 1,905,210 | A | * | 4/1933 | Bowers | 2/8.2 |
| 2,152,383 | A | * | 3/1939 | Leader | 2/8.2 |
| 2,152,865 | A | * | 4/1939 | Bowers | 2/8.1 |
| 2,461,548 | A | * | 2/1949 | Huntsman | 49/466 |
| 3,517,393 | A | | 6/1970 | Beauchef | |
| 3,577,563 | A | * | 5/1971 | Raschke | 2/8.1 |
| 4,853,973 | A | * | 8/1989 | Boochard | 2/8.1 |
| 5,533,206 | A | * | 7/1996 | Petrie et al. | 2/8.5 |
| 5,657,106 | A | | 8/1997 | Herald, Jr. et al. | |
| D393,933 | S | | 4/1998 | Huh | |
| 5,771,499 | A | | 6/1998 | Monaco et al. | |
| 6,038,707 | A | | 3/2000 | Ryden et al. | |
| 6,138,285 | A | | 10/2000 | Robrahn et al. | |
| 6,185,739 | B1 | * | 2/2001 | Verkic et al. | 2/8.1 |
| D446,887 | S | | 8/2001 | Young | |
| 6,450,639 | B1 | | 9/2002 | Abraham | |
| D478,111 | S | | 8/2003 | Huh | |
| D481,832 | S | | 11/2003 | Huh | |
| D482,502 | S | | 11/2003 | Huh | |
| D482,503 | S | | 11/2003 | Huh | |
| 6,973,672 | B2 | * | 12/2005 | Huh | 2/8.1 |

FOREIGN PATENT DOCUMENTS

KR  94-12068  6/1994
KR  20320527  7/2003

OTHER PUBLICATIONS

U.S. Appl. No. 10/062,510.

* cited by examiner

Primary Examiner—Katherine Moran
(74) Attorney, Agent, or Firm—W. Norman Roth

(57) ABSTRACT

Disclosed herein is a welding helmet having a cartridge coupling structure. The welding helmet comprises a helmet body configured to cover and protect the welder's head, an opening being formed at a front surface of the helmet body, a protective cover provided along a periphery thereof with a packing such as rubber, the packing having a protruding wing portion and serving to prevent harmful gas and foreign substances from reaching the inside surface of the protective cover, a cartridge coupled to the opening by interposing the protective cover and adapted to intercept intense light generated upon welding so as to protect the welder's eyes, and coupling elements to detachably couple the cartridge to the helmet body.

5 Claims, 4 Drawing Sheets

WELDING HELMET HAVING CARTRIDGE COUPLING STRUCTURE

BACKGROUND OF THE INVENTION

1. Field of the Invention

The present invention relates to a welding helmet having a cartridge coupling structure, and more particularly, to a welding helmet having a cartridge coupling structure, which can prevent fumes generated during welding or cutting from directly entering the welding helmet, in addition to protecting the wearer's face from intense light generated during welding or cutting, and can permit convenient exchange of a cartridge through easy attachment/detachment thereof.

2. Description of the Related Art

In general, arc welding is a technique to bond two metal pieces by locally heating and melting them using fusibility of metals. During welding, welders should wear welding helmets to protect their face from high heat, intense light and harmful gas generated during welding.

Conventionally, such welding helmets have been designed to have a handle piece for the manual operation thereof. However, this kind of welding helmet is troublesome in use since welders have to repeatedly put on the welding helmet whenever they perform welding.

As a result of continuous research and development for improving working efficiency of the welders, currently, welding helmets of the type using a band are commercialized.

The welding helmets, serving as protective equipment for use in welding or cutting, especially, have an anti-dazzling device (hereinafter, referred to as a cartridge) for protecting the welder's eyes from intense light caused by sparks discharged during welding or cutting. Such a cartridge is fixedly mounted to the welding helmets, and acts to intercept light having a wavelength more than 780nm and less than 365nm and control transmission of visible radiation, thereby allowing the welders to clearly see their work without a dazzling phenomenon during welding.

U.S. Pat. No. 5,533,206 discloses a welding helmet in which an easily removable electronic quick change (EQC) cartridge is retained in an integral cartridge housing. The EQC cartridge includes a liquid crystal display (LCD) lens, solar cells and photo sensor cells on its front side. The EQC cartridge is positioned on the front side of the welding helmet so that the LCD lens is positioned directly in front of the welder's eyes, thereby functioning as the actual viewing window. The solar cells absorb light and function as an energy input. The photo sensor cells detect sparks and other intense light and act as an input to a circuit that automatically adjusts the LCD lens to a variable opaque condition.

U.S. Pat. No. 6,070,264 discloses a welding helmet, which comprises a shutter through which a wearer of the helmet may view a welding operation, an electronic control associated with the shutter for controlling a light transmission shade of the shutter, a light sensor provided in the electronic control for sensing light emanating from the welding operation, and an electronic circuit provided in the electronic control for driving the shutter to a darker shade in response to the light sensor sensing brighter light from the welding operation.

However, the above-described conventional welding helmets have a problem in that their cartridges, which are used to detect intensity of light generated during welding and automatically drive the LCD lens or shutter to a darker shade according to the intensity of light so as to protect the welder's eyes, are impossible or difficult to remove from the welding helmets.

Another problem of the conventional welding helmets configured as stated above is that they have a fine gap at a coupling region between a helmet body and a cover member, thereby being incapable of preventing sparks and fumes generated during welding from entering the helmet body, resulting in a deterioration in the working efficiency of the welder.

SUMMARY OF THE INVENTION

Therefore, the present invention has been made in view of the above problems, and it is an object of the present invention to provide a coupling structure of a welding helmet and a cartridge, which can prevent fumes generated during welding or cutting from directly entering the welding helmet, in addition to protecting the wearer's face from intense light generated during welding or cutting, and can permit convenient exchange of the cartridge.

It is a further object of the present invention to provide a welding helmet having a cartridge coupling structure, in which a packing of material such as rubber, defining a stepped sealing structure having a protruding wing, is interposed between a cartridge and an opening formed in a helmet body.

It is another object of the present invention to provide a welding helmet, which includes a packing to absorb shock, applied from the outside or caused when the welding helmet falls to the ground, and employs a cartridge coupling structure that which receives hooks of a cartridge that are securely latched to fitting pieces protruding from the welding helmet so as to prevent the cartridge from being easily detached from the welding helmet due to the flexibility of the welding helmet.

It is yet another object of the present invention to provide a welding helmet having a cartridge coupling structure, in which a cartridge has a plurality of hooks protruding therefrom and having a bent-structured elastic leg hook form so as to be elastically pressed and latched to fitting pieces formed at an inner surface of the welding helmet.

The above and other objects can be accomplished by the provision of a welding helmet having a cartridge coupling structure comprising: a helmet body configured to cover and protect the welder's head, an opening being formed at a front surface of the helmet body; a protective cover provided along a periphery thereof with a packing, the packing having a protruding wing portion and serving to prevent harmful gas and foreign substances from reaching the protective cover; a light intercepting cartridge detachably coupled to the helmet body at the opening inside the protective cover and adapted to intercept intense light generated upon welding so as to protect the welder's eyes; and coupling elements to detachably couple the cartridge to the helmet body.

BRIEF DESCRIPTION OF THE DRAWINGS

The above and other objects, features and other advantages of preferred embodiments of the present invention will be more clearly understood from the following detailed description taken in conjunction with the accompanying drawings, in which.

DESCRIPTION OF THE PREFERRED EMBODIMENTS

Figure 1:
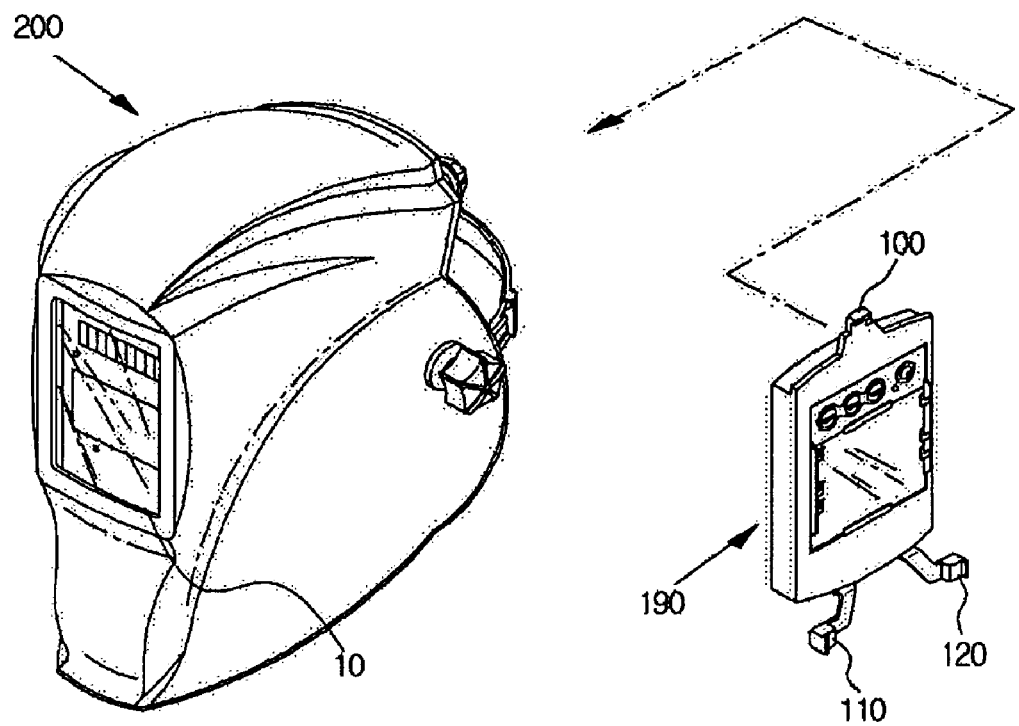
FIG. 1 is a perspective view illustrating a welding helmet and a cartridge in accordance with a preferred embodiment of the present invention.

Now, preferred embodiments of the present invention will be described in detail with reference to the annexed drawings.

FIGS. 1 to 4 illustrate a welding helmet and a cartridge in accordance with a preferred embodiment of the present invention.

As shown in FIGS. 1 to 4, the welding helmet according to the present invention comprises a helmet body 200 configured to cover and protect the welder's head, a cartridge 190 to be mounted in the helmet body 200, and a protective cover 40 to be interposed between the helmet body 200 and the cartridge 190. Here, a packing 30 is coupled to the protective cover 40 to surround the protective cover 40.

The helmet body 200 is made of lightweight material, such as self-extinguishing plastics, and has a rectangular opening 10 defined at a front surface thereof.

A fence 60 is formed at an inner surface of the helmet body 200 around the periphery of the opening 10. The fence 60 protrudes by a predetermined height and defines a fitting recess 50.

Inside the fitting recess 50 is inserted and coupled the cartridge 190, which is coupled to the protective cover 40 provided with the packing 30.

The packing 30 of the protective cover 40 is tightly fitted in the fitting recess 50 defined at the inner surface of the helmet body 200 and has a wing portion 20 protruding from a plane thereof facing the cartridge 190 so as to close a gap of the cartridge 190 when the protective cover 40 is coupled with the cartridge 190. Such a packing 30 prevents harmful gas and foreign substances from reaching the welder by passing around the protective cover 40, which comprises a transparent panel, while increasing sealing efficiency by virtue of the wing portion 20 thereof.

In the present invention, in order to facilitate coupling of the cartridge 190 relative to the helmet body 200, coupling elements are provided at the inner surface of the helmet body 200 around the opening 10 and at corresponding portions of the cartridge 190.

Figure 2:
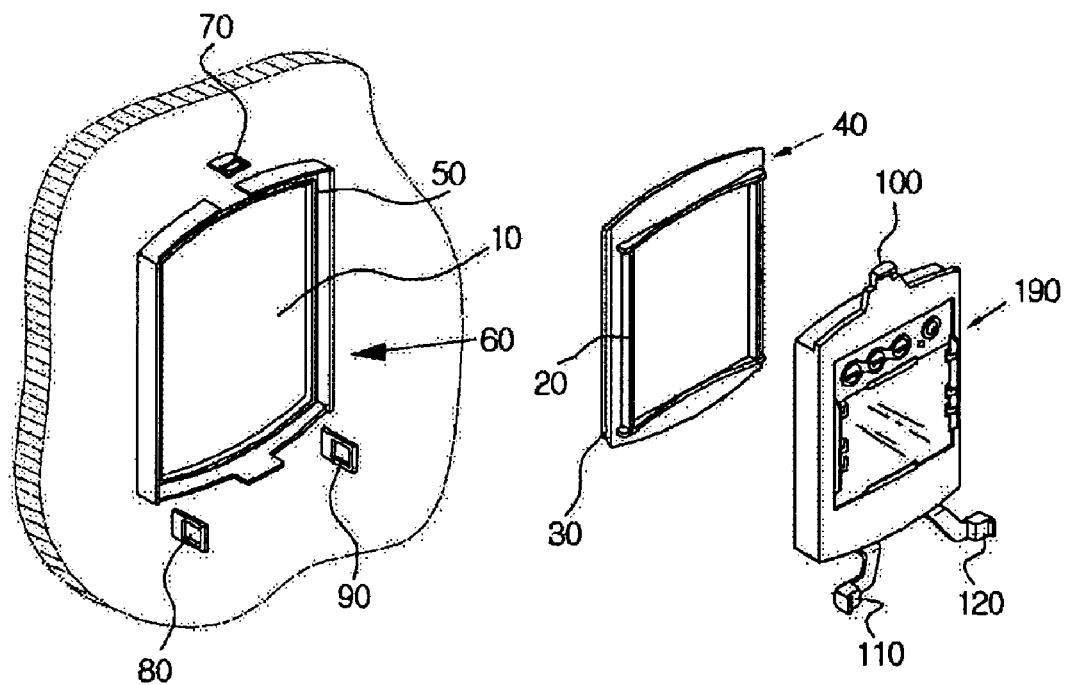
FIG. 2 is a perspective view illustrating associated coupling elements of the cartridge and the welding helmet shown in FIG. 1.
Figure 3:
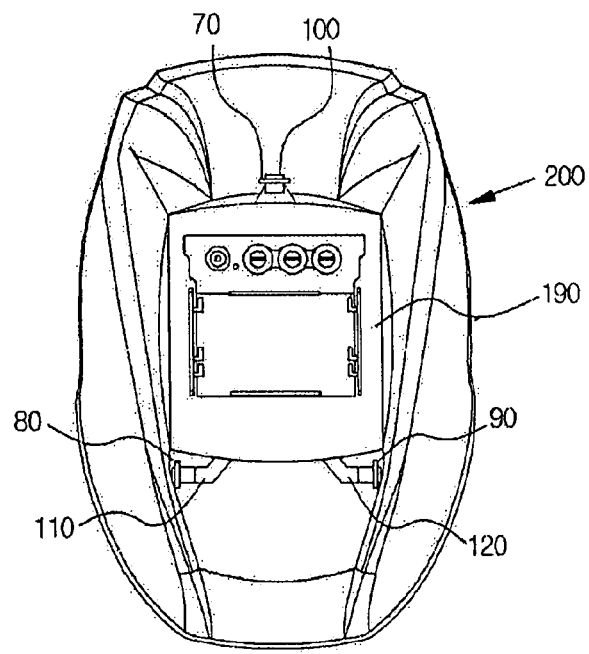
FIG. 3 is a rear view illustrating the welding helmet, which is installed with the cartridge shown in FIG. 1.
Figure 4:
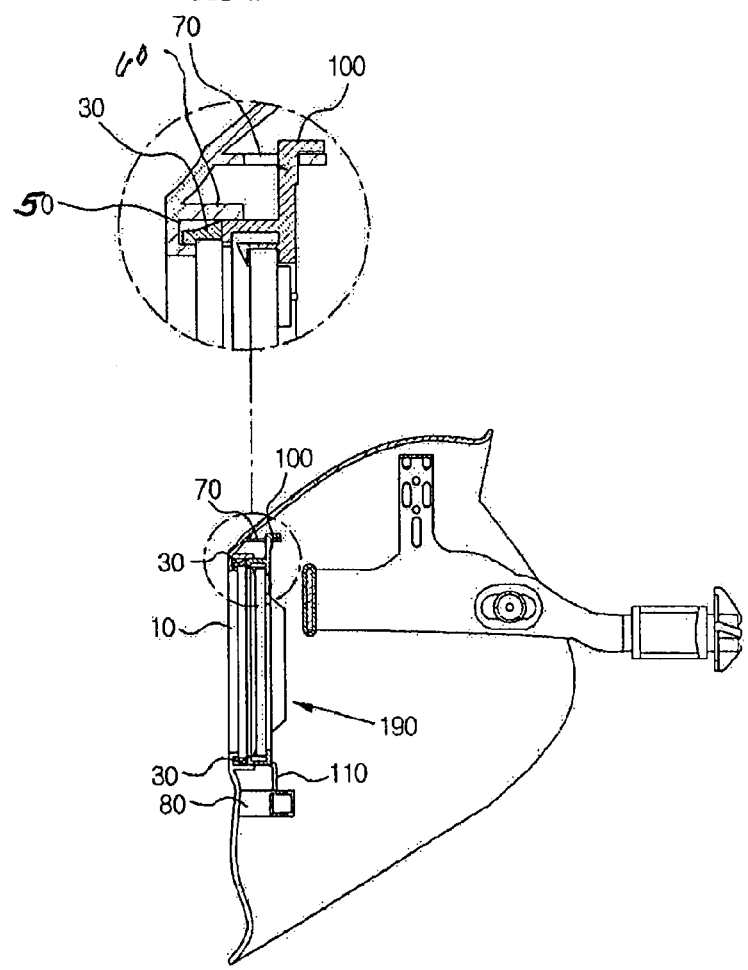
FIG. 4 is a side sectional view illustrating the coupling structure of the cartridge and the welding helmet shown in FIG. 1.

Explaining the elements for coupling the cartridge 190 to the helmet body 200 with reference to FIG. 2, above an upper end of the fence 60 is provided an upper fitting piece 70 to be positioned at the center of an inner surface of the helmet body 200. The fitting piece 70 protrudes toward the cartridge 190 to permit an upper hook 100 of the cartridge 190 to be latched upwardly thereto. Further, a pair of lower fitting pieces 80 and 90 is provided at opposite sides below a lower end of the fence 60 to permit a pair of lower hooks 110 and 120 to be latched laterally thereto. The lower hooks 110 and 120 of the cartridge 190 are bent-structured elastic leg hooks formed at a lower end of the cartridge 190.

The cartridge 190 has a rectangular panel form, and contains a photo sensor to sense intensity of light generated upon welding or cutting, a rechargeable solar battery to supply power required to drive the cartridge 190, an LCD panel adapted to be driven to a darker shade upon sensing a predetermined light intensity from the photo sensor so as to intercept intense light, a drive unit (not shown) to drive the LCD panel, a controller (not shown) to output driving signals to the drive unit if the photo sensor senses the predetermined light intensity, and a manual operator unit to permit manual adjustment of shade level. With such a configuration, the cartridge 190 acts to detect sparks and intense light caused during welding and drive the LCD panel to the darker shade according to the intensity of light, thereby protecting the welder's eyes from the intense light.

As described above, the cartridge 190 is detachably mounted inside the opening 10 of the helmet body 200. For such a detachable mounting, the cartridge 190 has the upper hook 100 and the lower elastic leg hooks 110 and 120 to be coupled to the fitting pieces 70, 80 and 90 of the helmet body 200, respectively.

The protective cover 40 is made of transparent resin panel, etc., and in order to prevent harmful gas and foreign substances from reaching the protective cover 40 made of the transparent panel, the packing 30 is fitted around the rim of the protective cover 40 made of the transparent panel and is fitted in the fitting recess 50 defined at the inner surface of the helmet body 200. In such a fitted state, the wing portion 20 of the packing 30, protruding from the plane of the packing 30 facing the cartridge 190, is tightly coupled to the cartridge 190.

Figure 5:
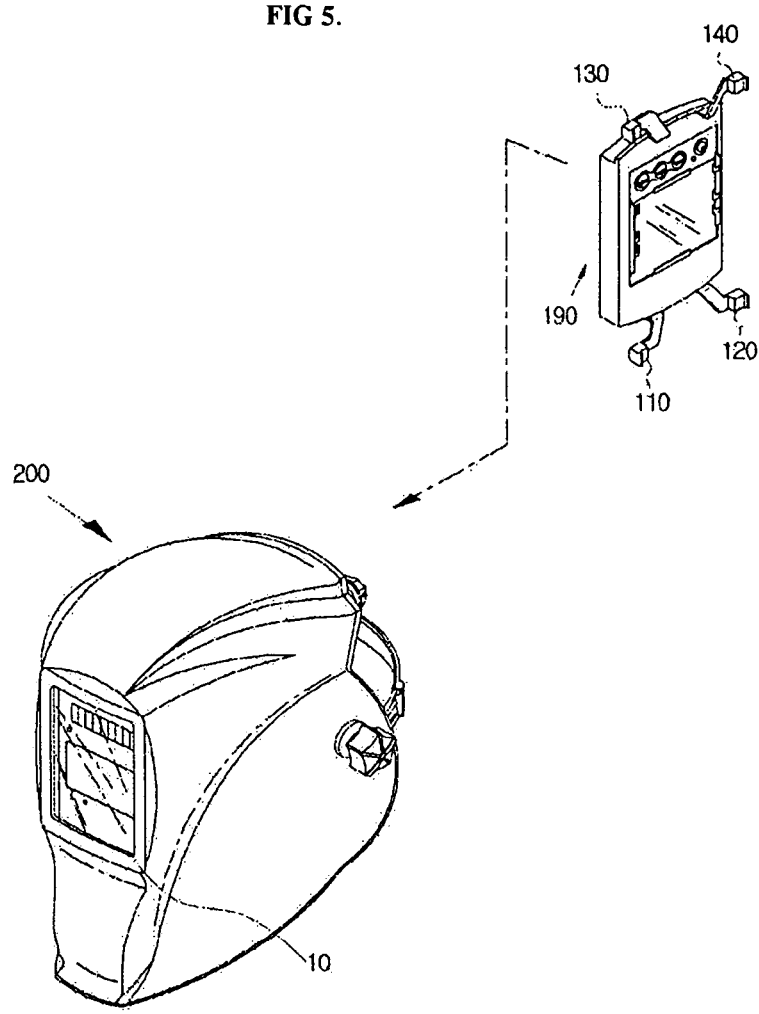
FIG. 5 is a perspective view illustrating a welding helmet and a cartridge in accordance with an alternative embodiment of the present invention.
Figure 6:
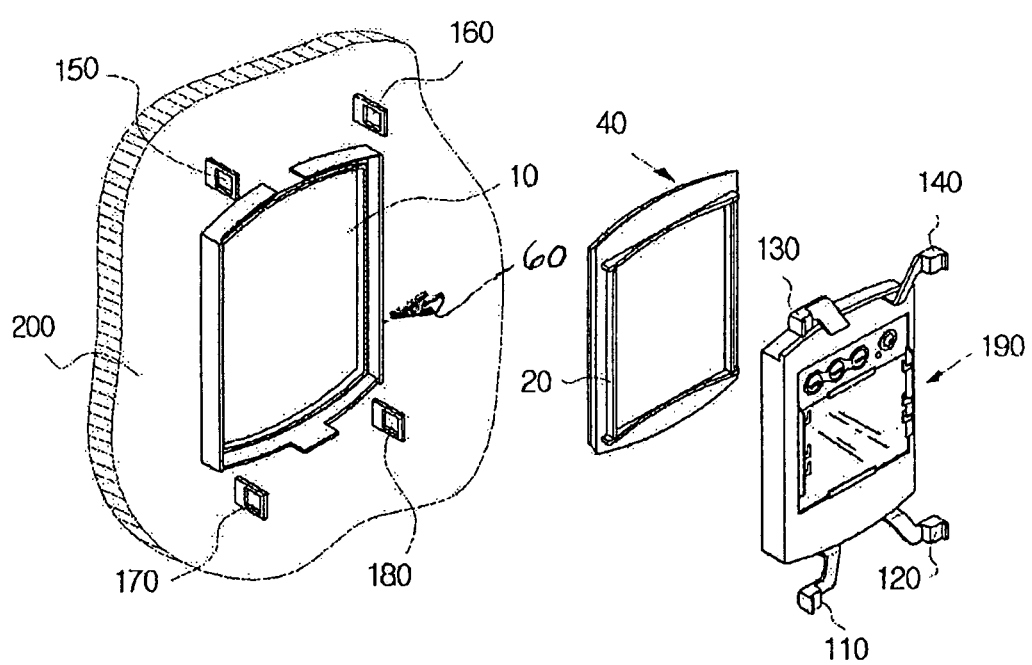
FIG. 6 is a perspective view illustrating associated coupling elements of the cartridge and the welding helmet shown in FIG. 5.
Figure 7:
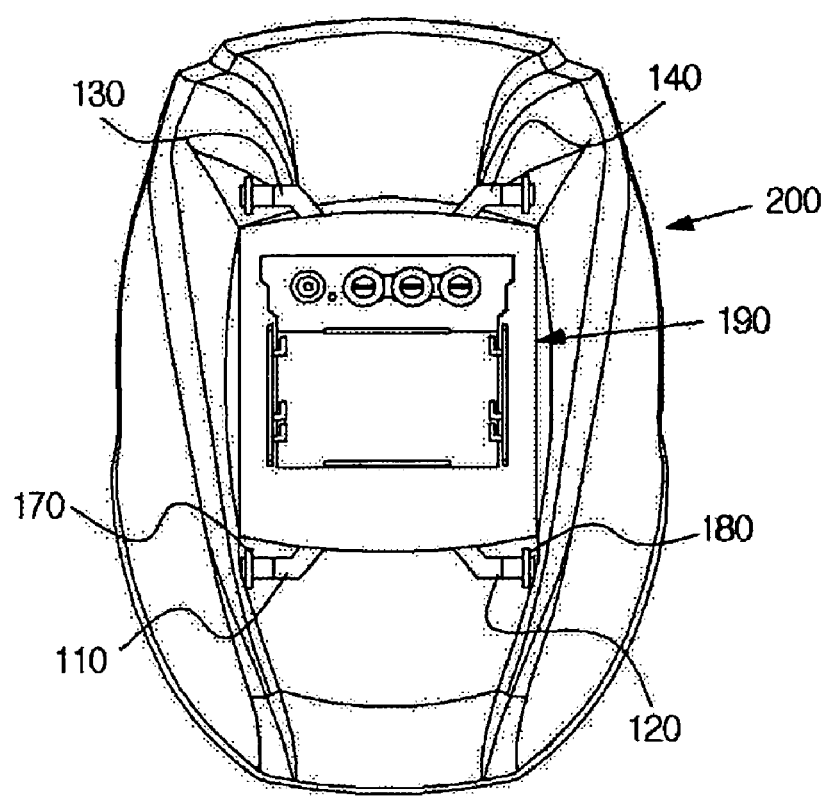
FIG. 7 is a rear view illustrating the welding helmet, which is installed with the cartridge shown in FIG. 5.

FIGS. 5 to 7 illustrate a welding helmet and a cartridge in accordance with an alternative embodiment of the present invention.

In the present embodiment, a pair of upper fitting pieces 150 and 160 and a pair of lower fitting pieces 170 and 180 are provided at opposite sides above the upper and lower ends of the fence 60 formed at the inner surface of the helmet body 200 around the opening 10.

To be latched to the upper and lower fitting pieces 150, 160, 170 and 180, the cartridge 190 of the present embodiment has a pair of upper elastic leg hooks 130 and 140 formed at an upper end thereof and a pair of lower elastic leg hooks 110 and 120 formed at a lower end thereof. These upper and lower elastic leg hooks 130, 140, 110 and 120 are bent to have elasticity. With such a configuration, the upper and lower elastic leg hooks 130, 140, 110 and 120 are able to be firmly latched to the corresponding fitting pieces 150, 160, 170 and 180, respectively, so as not to be unintentionally unlatched therefrom.

Now, the function of the welding helmet having the cartridge coupling structure configured as stated above will be explained in connection with the previous preferred embodiment of the present invention.

First, the protective cover 40, which is provided with the packing 30, is inserted in the fitting recess 50 defined at the inner surface of the helmet body 200 around the opening 10. Then, the cartridge 190 is coupled and assembled to a rear surface of the protective cover 40.

Thereby, the cartridge 190 is indirectly coupled relative to the helmet body 200 as it is coupled to the rear surface of the protective cover 40, which was coupled to the helmet body 200.

After that, in order to firmly fix the cartridge 190 to the helmet body 200, the upper hooks 130, 140 of the cartridge 190 are latched to the upper fitting pieces 150, 160 of the helmet body 200 in a state in which the cartridge 190 is coupled to the protective cover 40.

Then, the lower elastic leg hooks 110 and 120 of the cartridge 190, which are bent to have elasticity, are pressed to be latched to the fitting pieces 170 and 180, respectively.

After completing the coupling of the cartridge 190, the welding helmet is usable upon welding or cutting to protect the welder's head.

Meanwhile, during welding or cutting, harmful fumes are generated in addition to the intense light.

The fumes often directly reach the welder's face through a coupling portion between the cartridge and the helmet body, i.e. the opening of the helmet body. In the case of the welding helmet according to the present invention, the cartridge 190 is inserted in the fitting recess 50 defined by the fence 60, and is fixedly maintained as the upper hook 100 and the lower elastic leg hooks 110 and 120 thereof are latched to the fitting pieces 70, 80 and 90 of the helmet body 200, respectively, thereby completely preventing the fumes from directly entering the helmet body 200 through the opening 10 sealed by the packing 30.

When it is desired to repair or exchange the cartridge, the elastic leg hooks 110 and 120 of the cartridge 190 are first pressed, and then the fitting pieces 80 and 90 are moved away from each other, so as to permit the elastic leg hooks 110 and 120 to be unlatched from the fitting pieces 80 and 90. In this way, the cartridge 190 is detached from the welding helmet for the exchange thereof.

As stated above, the present invention provides a cartridge coupling structure using the hooks and fitting pieces, which permits easy exchange of the cartridge 190 while preventing unintentional separation of the cartridge 190 from the welding helmet possibly caused when flexibility of a material of the welding helmet is deteriorated. Upon exchange, the elastic leg hooks 110 and 120 are pressed and unlatched from the associated fitting pieces, thereby permitting easy separation of the cartridge 190.

As apparent from the above description, the present invention provides a welding helmet having a cartridge coupling structure, which permits convenient attachment/detachment of a cartridge relative to a helmet body.

Further, even if fumes are generated during welding or cutting, the welding helmet of the present invention can completely prevent the fumes from being entering the helmet body via an opening defined at the helmet body, resulting in outstanding merchantability in the industrial protective equipment.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A welding helmet having a cartridge coupling structure comprising:
   a helmet body configured to cover and protect the welder's head, an opening being formed at a front surface of the helmet body;
   a transparent protective cover having a packing along the periphery of the protective cover, the packing having a protruding wing portion whereby said packing serves to prevent harmful gas and foreign substances from reaching an inside surface of the protective cover;
   a cartridge coupled to the helmet body inwardly of the opening and the protective cover, said cartridge adapted to intercept intense light generated upon welding so as to protect the welder's eyes; and
   coupling elements to detachably couple the cartridge inside the helmet body.

2. The helmet as set forth in claim 1, wherein a fence is formed at an inner surface of the helmet body around a periphery of the opening to define a fitting recess.

3. The helmet as set forth in claim 1, wherein the packing is positioned in a formed at an inner surface of the helmet body so that the wing portion thereof, protruding from a plane facing the cartridge, is tightly coupled to the cartridge.

4. The helmet as set forth in claim 1, wherein the coupling elements include:
   an upper fitting piece protruding from the center of an inner surface of the helmet body above the opening and a pair of lower fitting pieces provided at the inner surface of the helmet body below the opening; and
   an upper hook formed at an upper end of the cartridge to be latched to the upper fitting piece and a pair of lower elastic leg hooks formed at a lower end of the cartridge to be latched to the lower fitting pieces, respectively, the lower hooks being bent to have elasticity.

5. The helmet as set forth in claim 1, wherein the coupling elements include:
   a pair of upper fitting pieces and a pair of lower fitting pieces protruding from an inner surface of the helmet body above and below the opening; and
   a pair of upper elastic leg hooks and a pair of lower elastic leg hooks formed at upper and lower ends of the cartridge to be latched to the upper and lower fitting pieces, respectively, the upper and lower hooks being bent to have elasticity.

* * * * *